United States Patent [19]
McAndrew et al.

[11] Patent Number: 5,963,336
[45] Date of Patent: Oct. 5, 1999

[54] CHAMBER EFFLUENT MONITORING SYSTEM AND SEMICONDUCTOR PROCESSING SYSTEM COMPRISING ABSORPTION SPECTROSCOPY MEASUREMENT SYSTEM, AND METHODS OF USE

[75] Inventors: James McAndrew, Lockport; Hwa-Chi Wang, Naperville; Benjamin J. Jurcik, Jr., Lisle, all of Ill.

[73] Assignee: American Air Liquide Inc., Walnut Creek, Calif.

[21] Appl. No.: 08/711,781

[22] Filed: Sep. 10, 1996

Related U.S. Application Data

[63] Continuation-in-part of application No. 08/634,449, Apr. 18, 1996
[60] Provisional application No. 60/005,013, Oct. 10, 1995.
[51] Int. Cl.$^6$ .......................... G01N 15/06; G01N 21/00
[52] U.S. Cl. .................. 356/437; 356/72; 216/60; 438/16
[58] Field of Search .................... 356/437, 440, 356/72; 216/60; 438/16

[56] References Cited

U.S. PATENT DOCUMENTS

| | | | |
|---|---|---|---|
| 3,524,066 | 8/1970 | Blakkan | 356/246 |
| 4,812,665 | 3/1989 | Puumalainen et al. | 250/571 |
| 4,857,136 | 8/1989 | Zajac | 216/60 |
| 4,934,816 | 6/1990 | Silver et al. | 356/440 |
| 4,937,461 | 6/1990 | Traina | 356/437 |
| 4,990,780 | 2/1991 | Lee et al. | |
| 5,045,703 | 9/1991 | Wieboldt et al. | |
| 5,047,639 | 9/1991 | Wong | |
| 5,065,025 | 11/1991 | Doyle | |
| 5,173,749 | 12/1992 | Tell et al. | 356/437 |
| 5,220,402 | 6/1993 | Harvey | 356/246 |
| 5,241,851 | 9/1993 | Tapp et al. | |
| 5,294,289 | 3/1994 | Heinz et al. | |
| 5,331,409 | 7/1994 | Thurtell et al. | |
| 5,352,902 | 10/1994 | Aoki | 250/575 |
| 5,453,621 | 9/1995 | Wong | |
| 5,459,574 | 10/1995 | Lee et al. | |
| 5,485,276 | 1/1996 | Bien et al. | |
| 5,517,314 | 5/1996 | Wallin | |
| 5,536,359 | 7/1996 | Kawada et al. | |
| 5,550,636 | 8/1996 | Hagans et al. | |
| 5,561,527 | 10/1996 | Krone-Schmidt et al. | |
| 5,578,829 | 11/1996 | Talasek et al. | |

FOREIGN PATENT DOCUMENTS

| | | |
|---|---|---|
| 0015170 | 9/1980 | European Pat. Off. |
| 0647845 | 4/1995 | European Pat. Off. |
| 0 706 042 | 4/1996 | European Pat. Off. |
| 0738887 | 4/1996 | European Pat. Off. |
| 144708 | 9/1980 | Germany |
| 3633931 | 4/1988 | Germany |
| 4214840 | 11/1993 | Germany |
| 25 04 300 | 11/1997 | Germany |
| 2075213 | 11/1981 | United Kingdom |
| 2165640 | 4/1986 | United Kingdom |
| WO90/00732 | 1/1990 | WIPO |
| WO94/24528 | 10/1994 | WIPO |

OTHER PUBLICATIONS

Kaur et al, "Multipass cell for molecular beam absorption spectroscopy," *Applied Optics,* Jan. 1, 1990, vol. 29, No. 1, pp. 119–124.

Fried et al, "Application of Tunable Diode Laser Absorption for Trace Stratospheric Measurements of CHI: Laboratory Results," *Applied Optics,* vol. 23, No. 11, Jun. 1, 1984, pp. 1867–1879.

Herriott et al., "Folded Optical Delay Lines", Applied Optics, vol. 4, No. 8, pp. 883–889 (Aug. 1965).

Inman et al, "Application of Tunable Diode Laser Absorption Spectroscopy to Trace Moisture Measurements in Gases," *Analytical Chemistry,* vol. 66, No. 15, pp. 2471–2479; Aug. 1994.

May et al, "Data Processing and Calibration for Tunable Diode Laser Harmonic Absorption Spectrometers," *J. Quant. Spectrosc. Radiat. Transfer,* vol. 49, No. 4, 1993, pp. 335–347.

May, "Computer Processing of Tunable Diode Laser Spectra," *Applied Spectroscopy,* vol. 43, No. 5, 1989, pp. 834–839.

Mucha et al., "Infrared Diode Laser Determination of Trace Moisture In Gases", ISA Transactions, vol. 25, No. 3, pp. 25–30 (1986).

Podolske et al, "Airborne Tunable Diode Laser Spectrometer for Trace–Gas Measurement in the Lower Stratosphere," *Applied Optics,* vol. 32, No. 27, pp. 5324–5333; Sep. 20, 1993.

Pokrowsky et al, "Sensitive Detection of Hydrogen Chloride by Derivative Spectroscopy with a Diode Laser," *Optical Engineering,* vol. 23, No. 1 (1984), pp. 088–091.

Riris et al, "Design of an Open Path Near–Infrared Diode Laser Sensor: Application to Oxygen, Water, and Carbon Dioxide Vapor Detection," *Applied Optics,* vol. 33, No. 30, Oct. 20, 1994, pp. 7059–7066.

Staab, "Industrielle Gasanalyze Industrial Gas Analysis," *Technisches Messen,* vol. 61, No. 3, Mar. 1, 1994, pp. 133–137.

White, "Long Optical Paths of Large Aperture", J. Opt. Soc. Am., vol. 32 (1942), pp. 285–288.

Wilson, "Modulation Broadening of NMR and ESR Line Shapes", J. App. Phys., vol. 34, No. 11, pp. 3276–3285 (1963).

R. Grisar et al, "Fast Sampling Devices for Dynamic Exhaust Gas Analysis," Proceedings of the 24th ISATA International Symposium on Automotive Technology and Automation, May 20, 1991, pp. 283–287.

A. Fried, "Versatile Integrated Tunable Diode Laser System for High Precision: Application for Ambient Measurements of OCS," *Applied Optics,* vol. 30, No. 15, May 20, 1991, pp. 1918–1932.

J.M. Jasinski et al, "Detection of $SiH_2$ in Silane and Disilane Glow Discharges by Frequency Modulation Absorption Spectroscopy," *Applied Physics Letters,* vol. 44, No. 12, Jun. 15, 1984, pp. 1155–1157.

P.B. Davies et al, "Infrared Laser Diagnostics in Methane Chemical–Vapor–Deposition Plasmas," *Journal of Applied Physics,* vol. 71, No. 12, Jun. 15, 1992, pp. 6125–6135.

T. A. Hu et al, "Improved Multipass Optics for Diode Laser Spectroscopy", Review of Scientific Instruments, vol. 64, No. 12, Dec. 1993, pp. 3380–3383.

Patent Abstracts of Japan, vol. 6, No. 59, JP 57–1953, Jan. 1982.

Fried et al., "Versatile Integrated Tunable Diode Laser System for High Precision: Application for Ambient Measurements of OCS", Applied Optics, vol. 30, No. 15, May 20, 1991, pp. 1916–1932.

May, "Correlation–Based Technique for Automated Tunable Diode Laser Scan Stabilization," Rev. Sci. Instrum., vol. 63, No. 5, May 1992; pp. 2922–2926.

Eng et al, "Tunable Diode Laser Spectroscopy: An Invited Review," Optical Engineering, Nov./Dec. 1980, vol. 19, No. 6; pp. 945–960.

Lundqvist et al, "Measurements of Pressure–Broadening Coefficients of NO and $O_3$ Using a Computerized Tunable Diode Laser Spectrometer," Applied Optics, vol. 21, No. 17, Sep. 1, 1982; pp. 3109–3113.

Ahlberg et al, "IR–Laser Spectroscopy for Measurement Applications in the Industrial Environment," TR 85170; Dec. 85.

Höjer et al, "Measurements of Electric Field Strength in Gas Insulated High–Voltage Components Using Infrared Diode Laser Absorption Spectroscopy," Applied Optics, vol. 25, No. 17; Sep. 1, 1986; pp. 2984–2987.

Cassidy, "Trace Gas Detection Using $1.3\mu m$ InGaAsP Diode Laser Transmitter Modules," Applied Optics, vol. 27, No. 2, Feb. 1, 1988; pp. 610–614.

Lichtman, "Residual Gas Analysis: Past, Present and Future", J. Vac. Sci. Technol. A8(3), pp. 2810–2813 (1990).

Dreyfus et al, "Optical Diagnostics of Low Pressure Plasmas," Pure & Appl. Chem., vol. 57, No. 9, pp. 1265–1276 (1985).

Smoak, Jr. et al, "Gas Control Improves EPI Yield", Semiconductor Int'l., pp. 87–92 (1990).

Feher et al, "Tunable Diode Laser Monitoring of Atmospheric Trace Gas Constituents," Spectrochimica Acta, A 51, pp. 1579–1599 (1995).

Webster et al, "Infrared Laser Absorption: Theory and Applications," Wiley, New York (1988).

Atkinson, "High Sensitivity Detection of Water Via Intracavity Laser Spectroscopy," Microcontamination Conference Proceedings, pp. 98–111 (1994).

Borden, "Monitoring Vacuum Process Equipment: In Situ Monitors—Design and Specification," Microcontamination, vol. 9, No. 1, pp. 43–47 (1991).

*Primary Examiner*—Robert H. Kim
*Assistant Examiner*—Zandra V. Smith
*Attorney, Agent, or Firm*—Burns, Doane, Swecker & Mathis, L.L.P.

[57] ABSTRACT

Provided is a novel chamber effluent monitoring system. The system comprises a chamber having an exhaust line connected thereto. The exhaust line includes a sample region, wherein substantially all of a chamber effluent also passes through the sample region. The system further comprises an absorption spectroscopy measurement system for detecting a gas phase molecular species. The measurement system comprises a light source and a main detector in optical communication with the sample region through one or more light transmissive window. The light source directs a light beam into the sample region through one of the one or more light transmissive window. The light beam passes through the sample region and exits the sample region through one of the one or more light transmissive window. The main detector responds to the light beam exiting the sample region. The system allows for in situ measurement of molecular gas impurities in a chamber effluent, and in particular, in the effluent from a semiconductor processing chamber. Particular applicability is found in semiconductor manufacturing process control and hazardous gas leak detection.

69 Claims, 4 Drawing Sheets

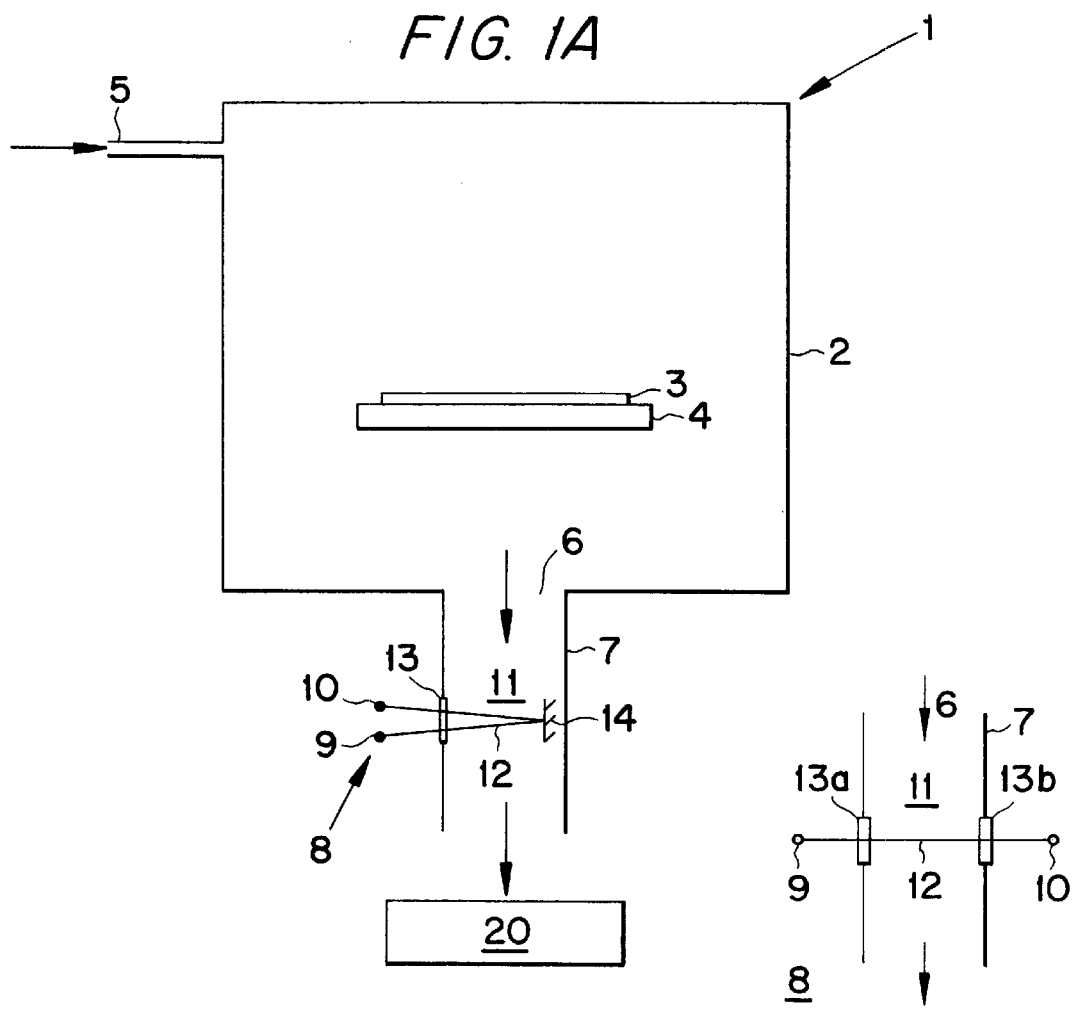
FIG. 1A
FIG. 1B
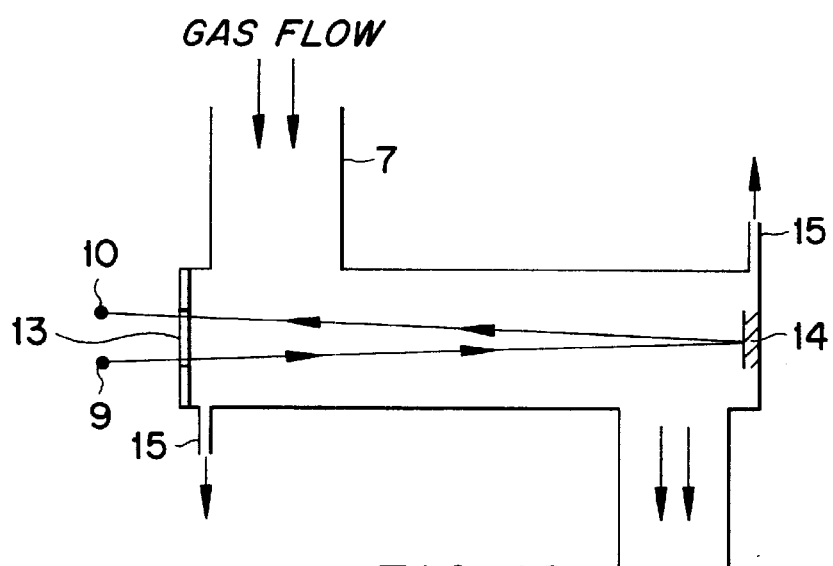
FIG. 1C

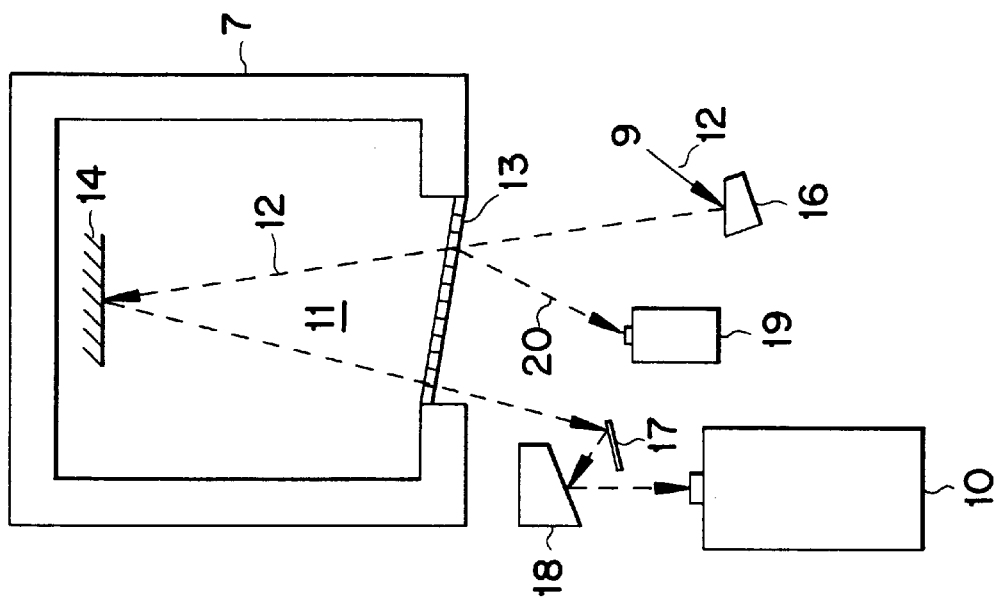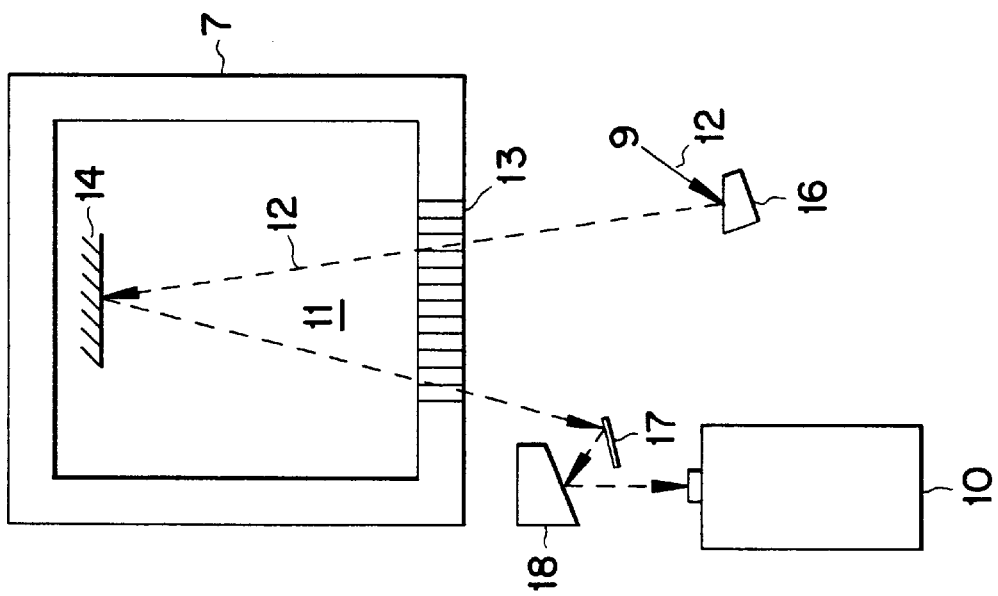

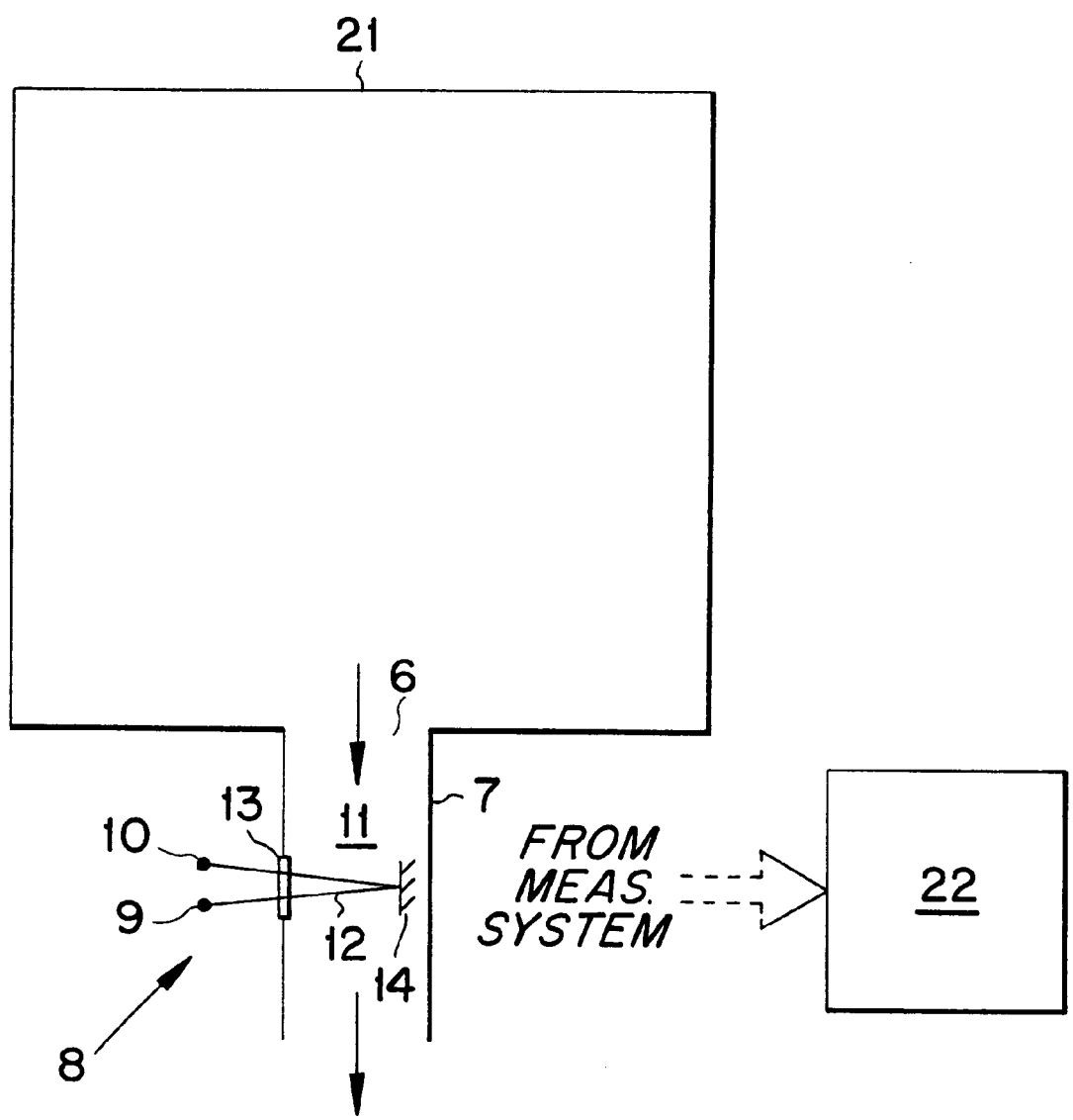

CHAMBER EFFLUENT MONITORING SYSTEM AND SEMICONDUCTOR PROCESSING SYSTEM COMPRISING ABSORPTION SPECTROSCOPY MEASUREMENT SYSTEM, AND METHODS OF USE

CROSS REFERENCE TO RELATED APPLICATIONS

This application is a Continuation-in-Part of application Ser. No. 08/634,449 filed on Apr. 18, 1996, and this application claims the benefit of U.S. Provisional Application No. 60/005,013 filed on Oct. 10, 1995.

BACKGROUND OF THE INVENTION

1. Field of the Invention

The present invention relates to a novel chamber effluent monitoring system and a semiconductor processing system which include an absorption spectroscopy measurement system for measuring a gas phase molecular species. The present invention also relates to a method of detecting a gas phase molecular species within the inventive chamber effluent monitoring system and inventive semiconductor processing system.

2. Description of the Related Art

In the manufacture of semiconductor integrated circuits (ICs), it is important to have an extremely low partial pressure of molecular impurities in the processing chamber. In particular, water vapor is especially detrimental to the devices fabricated in the processing tools. For example, water vapor must be eliminated or minimized in an aluminum etching chamber in order to achieve reproducible etching processes. Also, when subjected to water vapor during processing, corrosion of the device metallization layers is accelerated, substantially reducing product yield.

Molecular impurities may be introduced into the processing chamber in a number of ways. For example, molecular impurities may be present in the process gases introduced into the chamber during processing. Also, molecular impurities such as moisture are present in the air to which the chamber is exposed during maintenance of the processing tool. Air and water may also be introduced into the processing chamber whenever a substrate is introduced into the chamber. Molecular impurities may also be released from the substrates themselves after introduction into the process chamber or may result from the process conditions themselves. For example, during plasma processing and rapid thermal processing, molecular impurities may take the form of reaction byproducts or, as in the case of water vapor, may be released from substrate and chamber surfaces upon heating.

Molecular impurities which are introduced into the process chamber with a substrate are typically removed by purging the chamber with a pure gas, by evacuating the chamber, or by a series of pressurization-evacuation cycles.

In the case of chamber evacuation, the base pressure in the chamber is used as a measure of the extent of removal of the molecular impurities. Conversely, when relying on the chamber purge technique, the chamber is filled with a pure gas for a period of time which is usually determined by the operator's experience.

The extent of removal of atmospheric contamination from the processing chamber can also be determined by the measurement of water vapor concentration in the chamber. Such a technique is particularly useful in the case of contamination resulting from exposing the processing chamber to the outside atmosphere during maintenance and from introducing a substrate into the chamber. Water vapor can adhere to the surfaces inside a processing chamber as well as to the surface of the substrate. It is present in the atmosphere in an amount of from about 1–2%, and is generally the most difficult atmospheric constituent to remove by evacuation or purging.

In state-of-the-art production facilities, particle monitors are often used to monitor particulate contamination in situ. It is known to dispose particle monitors in the exhaust line of processing tools. (See, e.g., P. Borden, Monitoring Vacuum Process Equipment: In Situ Monitors—Design and Specification," Microcontamination, 9(1), pp. 43–47 (1991)). While such particle monitors may be useful for tracking process events which result in the generation of particles, they cannot be used to monitor molecular concentrations.

Among the analysis tools which can be used in the measurement of molecular contamination is one type of mass spectrometer, usually referred to as a residual gas analyzer (RGA). (See, e.g., D. Lichtman, Residual Gas Analysis: Past, Present and Future, J. Vac. Sci. Technol., A 8(3) (1990)). Mass spectrometers generally require pressures in the range of about $10^{-5}$ torr, whereas the operating pressures of semiconductor processing tools are often at pressures in the range of from about 0.1 to 760 torr. Consequently, mass spectrometers require sampling systems and dedicated vacuum pumps. Mass spectrometers are generally both expensive and not compact in construction. Moreover, the differentially pumped chamber in which the mass spectrometer is housed contributes a high level of residual water vapor which is difficult to remove and which severely limits the sensitivity of the mass spectrometer for water vapor measurement.

Optical emission spectroscopy is widely used for monitoring plasma processes. In principle, optical emission spectroscopy can be used to monitor molecular contamination in the processing tool. However, the optical emission spectrum is very complicated, and this method cannot be used in non-plasma processes.

Other spectroscopic techniques have been widely used in research situations to study process chemistry. (See, e.g., Dreyfus et al., Optical Diagnostics of Low Pressure Plasmas, Pure and Applied Chemistry, 57(9), pp. 1265–1276 (1985)). However, these techniques generally require specially modified process chambers and have not generally been applied to the study of contamination. For example, the possibility of in situ moisture monitoring by intracavity laser spectroscopy has been mentioned generally in a review of that technique. (See, e.g., G.W. Atkinson, High Sensitivity Detection of Water via Intracavity Laser Spectroscopy, Microcontamination, 94 Proceedings Canon Communications (1994)).

Finally, conventional gas analyzers have been applied to in situ moisture measurement, usually for processes running at or close to atmospheric pressure. (See, e.g., Smoak et al., Gas Control Improves Epi Yield, Semiconductor International, pp. 87–92 (June 1990)). According to such techniques, a portion of the process gas is extracted into a probe which then delivers the sample to the analyzer. However, use of a probe is undesirable in the measurement of moisture since moisture tends to adsorb on the surfaces of the probe. Moreover, this approach is often impractical as it requires considerable space to accommodate the conventional gas analyzers. It is well known that free space inside a semiconductor fabrication cleanroom is typically at a minimum.

A method for measuring the instantaneous moisture concentration and drydown characteristics of a processing environment is disclosed in U.S. Pat. No. 5,241,851, to Tapp et al. According to this method, a moisture analyzer alternately samples the effluent from a process chamber and the gas generated by a standard gas generator. The output of the standard gas generator is adjusted until the analyzer indicates no difference between the effluent and standard gas streams. Because the moisture content in the output of the standard gas generator is known, the level in the effluent stream can be determined. This system, however, is inconvenient and complicated as it requires a standard gas generator and complicated piping to effect switching between the effluent and standard gas streams. Moreover, there is a risk of backflow from the standard gas generator to the process chamber, resulting in contamination.

To meet the requirements of the semiconductor processing industry and to overcome the disadvantages of the prior art, it is an object of the present invention to provide a novel chamber effluent monitoring system, and in particular a novel semiconductor processing system, which includes an absorption spectroscopy system for detecting gas phase molecular impurities, which will allow for accurate, instantaneous and in situ determination of gas phase molecular impurities in a semiconductor processing tool.

It is a further object of the present invention to provide a method of detecting gas phase molecular species within the inventive chamber effluent monitoring and semiconductor processing systems.

Other objects and aspects of the present invention will become apparent to one of ordinary skill in the art on a review of the specification, drawings and claims appended hereto.

SUMMARY OF THE INVENTION

According to a first aspect of the present invention, a chamber effluent monitoring system is provided. The system comprises a chamber having an exhaust line connected thereto. The exhaust line includes a sample region, wherein substantially all of a chamber effluent also passes through the sample region.

The system further comprises an absorption spectroscopy measurement system for detecting a gas phase molecular species. The measurement system comprises a light source and a main detector in optical communication with the sample region through one or more light transmissive window. The light source directs a light beam into the sample region through one of the one or more light transmissive window, and the light beam passes through the sample region and exits the sample region through one of the one or more light transmissive window. The main detector responds to the light beam exiting the sample region.

In a second aspect of the invention, a semiconductor processing system is provided. The semiconductor processing system comprises a processing chamber for processing a semiconductor substrate. The processing chamber comprises an exhaust line connected thereto. The exhaust line includes a sample region, wherein substantially all of a chamber effluent passes through the sample region.

The processing system further comprises an absorption spectroscopy measurement system for measuring a gas phase molecular species as described above with reference to the chamber effluent monitoring system.

A third aspect of the invention is a method of detecting a gas phase molecular species in a chamber effluent. In the inventive method, a chamber is provided which has an exhaust line connected thereto. The exhaust line includes a sample region. Substantially all of a chamber effluent is removed from the chamber through the exhaust line and is passed through the sample region.

A gas phase molecular species is detected by an absorption spectroscopy method by directing a light beam from a light source into the sample region through one or more light transmissive window. The light beam passes through the sample region and exits the sample region through one of the one or more light transmissive window, and the light beam exiting the cell through one of the one or more light transmissive window is detected.

The novel systems and methods permit accurate, instantaneous and in situ detection of gas phase molecular species in a chamber effluent. Particular applicability can be found in semiconductor manufacturing process control and in hazardous gas leak detection. For example, the time dependent moisture concentration and drydown characteristics of a semiconductor process environment can be monitored.

BRIEF DESCRIPTION OF THE DRAWINGS

The objects and advantages of the invention will become apparent from the following detailed description of the preferred embodiments thereof in connection with the accompanying drawings in which like numerals designate like elements, and in which:

FIGS. 1A, 1B and 1C are side-sectional views of chamber effluent monitoring systems according to the present invention;

FIGS. 2A and 2B are cross-sectional views of chamber effluent monitoring systems according to the present invention;

FIG. 5 is a cross-sectional view of chamber effuent monitoring systems according to further aspects of the invention.

DETAILED DESCRIPTION OF THE PREFERRED EMBODIMENTS OF THE INVENTION

Figure 3:
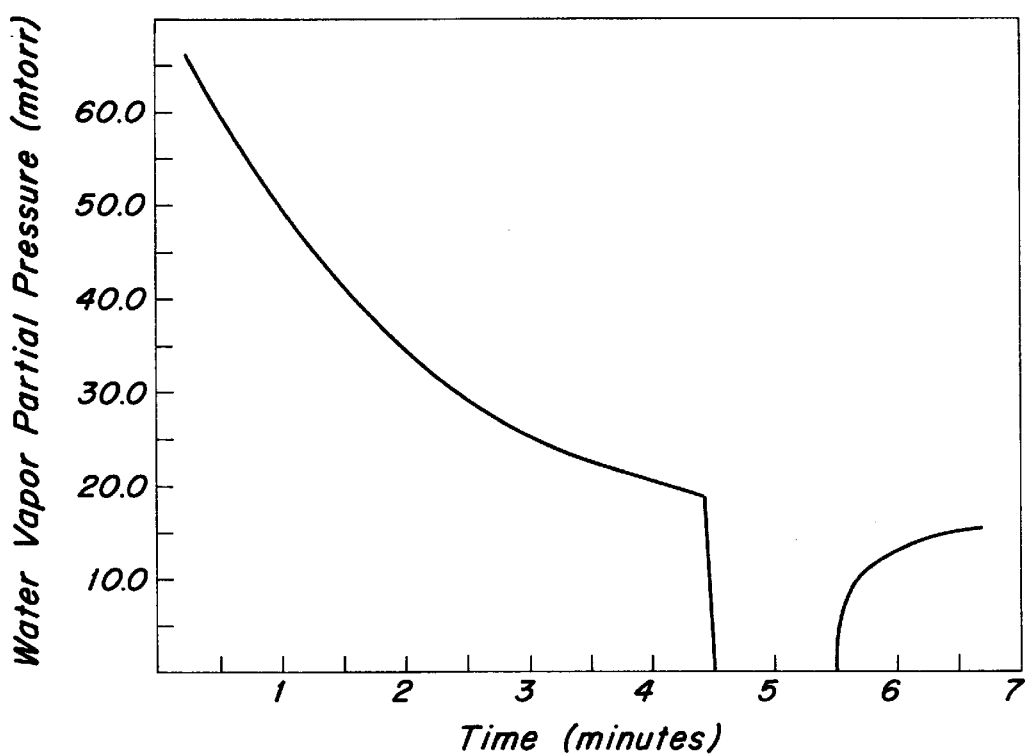
FIG. 3 is a graph of water vapor concentration versus etching process time in accordance with Example 1.

The above objectives of the present invention have been realized through the use of a spectroscopic method to measure molecular gas phase species in a chamber effluent, wherein substantially the entire flow of effluent gas from the chamber is directed through a spectroscopic sample region. In this way, measurements which follow changes in the actual impurity content in the effluent can be made very quickly.

As used herein, the terms "molecular gas phase species," "molecular impurity" and "contamination" are considered equivalent terms, and refer to a molecular gas or vapor species which is the object of the absorption spectroscopy measurement. Also, as used herein, the term "substantially the entire flow of effluent" means about 90–100% by volume of the total effluent flow from the chamber.

The invention will now be described with reference to FIGS. 1A and 2A, which illustrate side-sectional and cross-sectional views, respectively, of an inventive chamber effluent monitoring system.

System 1 comprises a semiconductor processing chamber 2, inside which a semiconductor substrate 3 is disposed on a substrate holder 4. A gas inlet 5 is provided for delivering a process gas or plural gases to processing chamber 2. Effluent from processing chamber 2 is exhausted through an exhaust opening 6 in processing chamber 2 and through an exhaust line 7 which can be connected to a vacuum pump, a fan or a scrubber system 20.

According to one aspect of the invention, the processing system is suitable to run vacuum processes, such as etching, sputtering, ion implantation or chemical vapor deposition (CVD) processes. In such a case, processing chamber 2 is a vacuum chamber, and a vacuum pump (not shown) can be connected to the exhaust line 7. The vacuum pump can be connected to another pump and/or to a gas scrubber (not shown). Examples of vacuum pumps which may be employed in these processes are mechanical rotary and booster pumps, diffusion pumps, cryogenic pumps, sorption pumps and turbomolecular pumps. Alternatively, the processing system can run processes such as atmospheric pressure CVD, wherein processing chamber 2 is held at about atmospheric pressure with a slight vacuum.

The processes often call for reactive or nonreactive (inert) gas species which can be in a plasma- or non-plasma state. Examples of reactive gases which can be used in the inventive system include $SiH_4$, $HCl$ and $Cl_2$, provided the moisture level is less than 1000 ppm. However, the reactive gases are not limited to these. Any inert gas such as, e.g., $O_2$, $N_2$, Ar and $H_2$ can be used in the inventive system.

In order to detect and measure molecular gas phase impurity concentrations in the processing tool, the inventive semiconductor processing system further includes an absorption spectroscopy measurement system 8 for measuring a gas phase molecular species. The absorption spectroscopy measurement system comprises a light source 9 and a detector 10, which can be a photodiode, in optical communication with a sample region 11 in exhaust line 7.

Any molecular impurity of interest can be detected, subject only to the availability of a suitable light source. For example, water vapor, nitric oxide, carbon monoxide and methane or other hydrocarbons can be detected by measuring the attenuation of light from a diode laser source which emits light of a wavelength characteristic of the impurity.

Laser light sources which emit light in spectral regions where the molecules of interest absorb most strongly lead to improvements in measurement sensitivity. In particular, light sources which emit at wavelengths longer than about 2 $\mu$m are preferred, since many of the molecular impurities of interest have strong absorption bands in this region.

Any suitable wavelength-tunable light source can be used. Of the currently available light sources, diode laser light sources are preferred because of their narrow linewidth (less than about $10^{-3}cm^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (i.e., wavelength greater than 3 $\mu$m), while the GaAs-type diode laser can operate at close to room temperature and emits in the near infrared region (0.8–2 $\mu$m).

Recently, diode lasers which include Sb in addition to GaAs (or other pairs of III-V compounds such as AsP) have been described (see, "Mid-infrared wavelengths enhance trace gas sensing," R. Martinelli, Laser Focus World, March 1996, p. 77). These diodes emit light of a wavelength greater than 2 $\mu$m while operating at $-87.8°$ C. While such a low temperature is not convenient, it compares favorably with the cryogenic temperatures (less than $-170°$ C.) required by Pb-salt lasers. Operation of similar lasers at 4 $\mu$m and 12°C. has also been reported (see, Lasers and Optronics, March 1996). Diode lasers of the above described type will most preferably operate at temperatures of at least $-40°$ C. Use of a thermoelectric cooler for temperature control at such temperatures makes these light sources less complicated than the lower temperature diode systems. To make use of these lasers more desirable, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

Light beam 12 which is generated by the described light source 9 is transmitted into sample region 11 through at least one light transmissive window 13, which can be disposed in the wall of exhaust line 7. The measurement system can be configured such that light beam 12 is reflected by a light reflective surface 14 within the sample region and exits sample region 11 through the same window it enters the sample region through. Alternatively, the windows through which the light beam enters and exits the sample region can be different and can be disposed on different sides of the exhaust line, for example, as illustrated in FIG. 1B, which shows light beam 12 passing through first light transmissive window 13a before entering the sample region 11, and the light beam passing through second light transmissive window 13b after passing through the sample region. In this exemplary embodiment, the light path between the first and second light transmissive windows is substantially linear. The measurement system can also be configured such that the light beam passes straight through the sample region from a light inlet window through a light exit window without being reflected in the sample region.

Light reflective surface 14 can be formed either separate from or integral with a wall of exhaust line 7.

Light reflective surface 14 is preferably a polished metal. As a high reflectivity of this surface is desirable, the surface can be coated with one or more layers of a reflective material such as gold, other metallic layers or a highly reflective dielectric coating in order to enhance the reflectivity thereof. Moreover, to minimize the adverse effects created by deposits formed on the light reflective surfaces, a heater for heating the light reflective surface can also be provided.

With reference to FIG. 1C, when the spectroscopy measurement is made in a portion of the exhaust line which is not connected to the chamber by a straight line, but rather is connected to the chamber after a bend in the line, it has been determined that removal of a small portion of the exhaust at the bend is particularly advantageous in that the fluid dynamics in the measurement region are enhanced considerably. A bend in the exhaust line upstream from the sample region results in eddies which are relatively slow to respond to upstream concentration changes.

In such a case, a fluid stabilizing amount of exhaust can be removed through fluid stabilization line(s) 15. In so doing, the eddies can be effectively eliminated or minimized. The amount of effluent removed from through fluid stabilization line 15 is less than about 10% by volume of the total effluent flow from the chamber.

In reference to FIGS. 2A, the absorption spectroscopy measurement system 8 can further include at least one first mirror 16 for reflecting light beam 12 from light source 9 through light transmissive window 13 into sample region 11, and at least one second mirror 17, 18 for reflecting light beam 12 exiting sample region 11 to main detector 10. Mirror 16 is preferably curved in order to collimate the light beam as the light from the diode laser source is divergent. Likewise, mirrors 17, 18 are preferably curved in order to focus the parallel light beam on detector 10.

In a further embodiment of the invention, illustrated in FIG. 2B, the angle of light transmissive window 13 can be adjusted such that the incident angle of the laser light can be increased or decreased away from an angle normal to the window. This feature is particularly advantageous because reflection of the laser light back to the laser can be adjusted and minimized. Such back reflection can both increase laser noise (e.g., by feedback into the cavity) or lead to interference fringes (e.g., by forming an etalon with the laser facets) which reduce measurement sensitivity.

Disposing window 13 at an angle conveys a further advantage in that a second detector 19 can be conveniently utilized for detection of the reflected portion of the incident light beam. It should be noted that the figures are not drawn to scale, and in practice window 13 can be made as small as required. Also, the angle between the incident light beam and the reflected light beam from mirror 14 is, in practice, smaller than indicated. Thus, the importance of angling the window 13 is greater than might appear from a very casual inspection of FIGS. 2A and 22.

Light transmissive window 13 can additionally be provided with a coating layer on a surface opposite the surface facing the sample region for reflecting a portion of light beam 12. Subtracting the signal due to the reflected portion of the beam from that of the transmitted portion can result in more accurate absorption measurements. Among the commercially available coating materials, metallic coatings are preferred. Suitable coated windows are commercially available from various suppliers such as Oriel, Melles Griot, and Newport.

A second detector 19, which can also be a photodiode, for measuring a portion 20 of the light beam which is reflected from light transmissive window 13 as well as means for subtracting this reference signal from a measurement obtained by main detector 10 can optionally be provided in the system. An operational amplifier in a configuration such as described in the literature (See, e.g., Moore, J. H. et al., *Building Scientific Apparatus*, Addison Wesley, London, (1983)) can act as the means for subtracting the reference signal.

The reflected light does not show any absorption by the molecules of interest in the sample region, and therefore provides a reference signal. By subtracting the reference signal from that of the light which passes through the cell (which is measured by the main detector), variations in the light source can be compensated for. This also allows for enhanced sensitivity to signal changes due to the molecular species in the processing chamber 2. While "dual beam" techniques using subtraction of a reference beam are wellknown, they usually require a dedicated beam-splitter, i.e., an optical element whose only function is to divide the light beam. According to the present invention, the entrance window to the chamber can provide this function without the need for any additional components. The ratio of transmitted to reflected light at this window can be controlled by use of an appropriate coating for the window.

The light source is preferably a diode laser maintained at a precisely controlled temperature. The temperature of the diode laser is generally controlled with a precision of at least plus or minus 0.1° C. Suitable diode lasers and temperature controllers are well known in the art and are available from several manufacturers. Lead salt lasers are available from the Laser Analytics Division of Laser Photonics Corp., and GaAs lasers are available from Sensors Unlimited, Inc. A suitable temperature controller is the Lake Shore DRC-910A temperature controller (for cryogenic temperatures) or any of several models from ILX Lightwave, Inc. for near room temperature operation.

Light source electronics control the current applied to the diode laser such that the diode laser emits light of a specific wavelength which is absorbed by the molecular impurity desired to be measured. As current applied to the laser diode increases, wavelength increases or decreases depending on the diode type. Laser current controllers are known in the art and commercially available. A suitable controller is the ILX Lightwave LDX-3620.

A detector, such as a photodiode, responds to light of the same wavelength as emitted by the diode laser. Suitable detectors are known in the art and commercially available, such as the Graseby HgCdTe Model 1710112 for infrared detection, or the EG&G InGaAs C30641 for near infrared detection, with a 10-MHz bandwidth amplifier. Detector 10 responds to light beam 12 which is reflected from a surface within the exhaust line and exits the sample region through one of the one or more light transmissive window 13. Detector electronics receive the output from the detector and generate an output which is related to the absorbance of light at the desired wavelength. The absorbance, i.e., the ratio of the detected light intensity in the presence of the molecular impurities of interest to the intensity which would be observed in their absence, can be converted into a concentration of the molecular impurities by a computer using known calibration data.

Various methods for controlling the wavelength of the light emitted by the diode laser can be used. For example, the laser wavelength may be locked to the desired value by a feedback system or may be repetitively swept over a region which includes the desired wavelength in order to generate a spectrum. Subsequent spectra may be averaged to improve sensitivity. Both of these techniques are known. (See, e.g., Feher et al., Tunable Diode Laser Monitoring of Atmospheric Trace Gas Constituents, Spectrochimica Acta, A 51, pp. 1579–1599 (1995) and Webster et al., Infrared Laser Absorption: Theory and Applications, Laser Remote Chemical Analysis, R. M. Measuews (Ed.), Wiley, New York (1988)). A further method for stabilizing wavelength is disclosed in copending application, Ser. No. 08/711,780 filed on even date herewith, which hereby incorporated by reference.

Further improvements in sensitivity can be achieved by modulating the diode current and wavelength and demodulating the detector signal at the modulation frequency or one of its higher harmonics. This technique is known as harmonic detection spectroscopy. (See, Feher et al., Tunable Diode Laser Monitoring of Atmospheric Trace Gas Constituents, Spectrochimica Acta, A 51, pp. 1579–1599 (1995) and Webster et al., Infrared Laser Absorption: Theory and Applications in Laser Remote Chemical Analysis, R. M. Measuews (Ed.), Wiley, New York (1988)).

As disclosed in copending application, Ser. No. 08/711, 646, filed on even date herewith, which is hereby incorporated by reference, in a particularly effective harmonic detection absorption system, the light source modulation amplitude can be set to a value which approximately maximizes the value of a harmonic signal at the center of the absorption feature being detected. In this system, the light source and detector are contained within a chamber which is isolated from the sample region, and the chamber pressure is controlled to a pressure greater than atmospheric pressure. By pressurizing the chamber, the detected signal can be maximized, thereby providing accurate measurements in a sample as low as in the parts per billion (ppb) range.

In another embodiment of the invention, a plurality of mirrors (or one mirror having multiple faces) can be disposed within the exhaust line 7. This allows the light beam to pass through the sample region a plurality of times. By increasing the effective pathlength in this manner, sensitivity of the measurement system is thereby enhanced.

Various forms of multipass optics are disclosed in copending application Ser. No. 08/711,504, filed on even date herewith, which is hereby incorporated by reference. As disclosed in this copending application, multipass cells are able to improve sensitivity of the measurement system by extending the effective pathlength the light beam travels. Among these cells, the planar multipass cell can be made arbitrarily small in directions parallel and perpendicular to the plane of propagation of the light. Because of its size, the planar multipass cell is particularly well suited for use in existing semiconductor processing tools.

The particular cell featured in that application is a polygonal planar multipass cell. The cell comprises a sample region circumscribed by a plurality of walls with light reflective surfaces. As a result of the regular shape, the light beam can be reflected by each wall prior to exiting the cell. Because the light beam can remain in the same plane, the size of the cell can be kept to a minimum.

The following example illustrate that the systems and methods of the invention are particularly beneficial in the detection of gas phase molecular species.

EXAMPLE 1

As described below, moisture concentration in a semiconductor processing system during etching is monitored, using the operating procedure described below.

As the semiconductor processing system, an Applied Materials Precision 5000 plasma etching system is used in conjunction with a TDLAS measurement system. The measurement system is set up for water vapor measurement to determine the drydown characteristics of the processing chamber.

The measurement system sample region is disposed in the exhaust line of the etching tool. The light transmissive inlet and outlet windows are disposed directly across from each other in the walls of the exhaust line, with the sample region disposed therebetween, such that the light emitted by the laser diode passes straight through the inlet window to the outlet window.

The diode is manufactured by Sensors Unlimited Inc., and is composed of InGaAsP/InP. The diode is fabricated in order to emit light in the wavelength region including 1.3686 micrometer where a strong absorption by water vapor occurs. The diode should is of the distributed feedback (DFB) type, ensuring single mode emission, i.e., to ensure that the diode emits at a single frequency, as described in M. Feher et al, Spectrochimica Acta A 51 pp. 1579–1599 (1995). The diode is mounted on a thermoelectric cooler which is controlled to 2511° C. by a Hytek 5610 subminiature proportional temperature controller. The laser current is controlled by an ILX Lightwave ILX 3620.

The diode is placed at the focus of a 0.5 inch diameter off-axis paraboloid mirror which collimates the diode laser beam. The mirror has a polished aluminum surface. The detector is an EG&G C30642 which is a 2 mm active diameter InGaAs photodiode. The detector output is amplified by an Analog Modules Inc. pre-amplifier. The system is extremely compact, and (except for the current controller) can be accommodated in a cube about 6 inches on each side.

The wavelength of the light emitted by the laser diode is locked to the characteristic value (i.e., 1.3686 um) using a feedback signal to the laser diode. To properly lock onto the wavelength, a signal corresponding to the third derivative of the absorption signal is used. Moisture measurements are initiated upon entry of the substrate into the processing chamber and are terminated upon completion of the process, with measurements being averaged over one second intervals. The data are instantaneously calculated, with the results being fed back to the etching tool process controller.

After loading the semiconductor substrate into the processing chamber, the system is evacuated until the water vapor partial pressure is 20 mtorr. At this point, 30 sccm $BCl_3$, 40 sccm $Cl_2$, 250 sccm He and 9.4 sccm $CHCl_3$ are introduced into the processing chamber. After one minute, the gas flows are shut off and the moisture level gradually recovers to approximately its previous level following reaction with residual $BCl_3$.

FIG. 3 is a graph of water vapor pressure versus processing time. The moisture partial pressure drops below detectable levels because of the rapid reaction of $BCl_3$ With water vapor as follows:

$$2BCl_3 + 3H_2 = B_2O_3(solid) + 6HCl$$

Thus, adding $BCl_3$ too early in the process, when the moisture partial pressure is too high, is disadvantageous since an excessive quantity of particles will be formed. Particles are well-known to have deleterious effects on the semiconductor devices. On the other hand, the presence of water vapor during several etch processes, such as aluminum etching, is intolerable. $BCl_3$ is therefore necessary in order to eliminate the last vestiges of water vapor. The inventive system can be used to determine when the moisture partial pressure is sufficiently low to permit $BCl_3$ addition and also to verify that the addition of $BCl_3$ is sufficient to completely remove vestigial water vapor.

EXAMPLE 2

Using the same etching tool described above in reference to Example 1, CO is monitored in a plasma ASH process wherein photoresist from an etched substrate is stripped. In the measurement system, a Pb-salt diode manufactured by Laser Photonics Corp. is mounted in a Laser Analytics liquid nitrogen-cooled coldhead. A one inch diameter, aspheric, antireflective coated, F/1 ZnSe lens is used to collimate the beam. The detector is a Graseby HgCdTe Model 1710112, with a 10-MHz bandwidth amplifier. Laser current is controlled by an ILX Lightwave LDX-3620, and the temperature is controlled by a Lake Shore DRC-910A controller. The wavelength of the light emitted by the laser diode is locked to the characteristic value for CO, i.e., 4.7 $\mu$m, using a feedback signal to the laser diode. A signal corresponding to the third derivative of the absorption signal is used.

After loading the semiconductor substrate into the etching chamber, $O_2$ at a flow rate of 60 sccm is introduced into the chamber. The pressure is maintained at 1.5 Torr during processing, and the CO measurements are performed throughout processing. Measurements are averaged over one second intervals.

Figure 4:
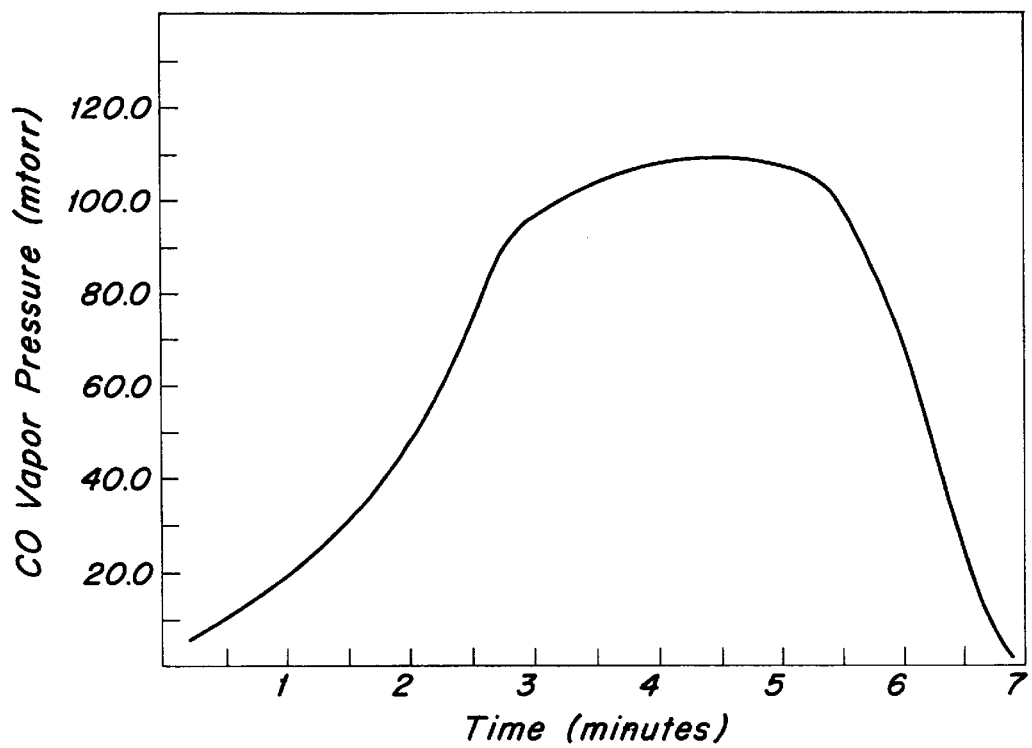
FIG. 4 is a graph of carbon monoxide concentration versus etching process time in accordance with Example 2.

The results from the CO measurement are set forth in FIG. 4, showing CO vapor pressure versus processing time. The graph indicates that the endpoint of the process occurs after about 6 minutes, at which point the CO in the processing chamber drops off.

The above examples show that the inventive system and method are well suited for monitoring gas phase molecular species in an exhaust line.

In addition to the above applications, the invention is particularly applicable to use in a load-lock chamber. Whenever a wafer is introduced into a semiconductor processing chamber, it is generally first placed in a load-lock chamber, which is purged and/or vacuum cycled in order to remove atmospheric air and other contaminants. The wafer is then transferred from the load-lock chamber to the process chamber itself. The extent of purging and/or vacuum cycles required may be determined by the pressure attained in the vacuum cycle. However, this is not a specific measurement and does not indicate whether the residual pressure is primarily due to water vapor (usually a result of substrate exposure to air), or to other species outgassing from the substrate (usually from previous process steps). Thus, it is particularly beneficial to monitor water vapor in load-lock chambers. Such a method is especially useful for load-locks relying solely on purging, since vacuum measurement is not feasible.

By disposing a diode laser system on the exhaust line of a load-lock chamber, it is possible to measure water vapor in the load lock effluent after purge cycling. If the required moisture level in the process is known, the purging time can be optimized to be just sufficient to provide the requisite purity. As transfer steps between processes are known to account for a significant fraction of available process chamber time in the semiconductor industry, significant cost advantages can be realized by this procedure.

In a similar way, a moisture sensor placed on the exhaust of any chamber can be used to optimize the length of an initial purge or vacuum cycle, which is often used to eliminate atmospheric constituents after loading wafers from the clean room, a previous process step, a load-lock chamber, or a transfer chamber.

While the invention has been described in reference to a semiconductor processing tool, persons of ordinary skill in the art will readily appreciate that the inventive system can also be adapted to a variety of different applications. For example, it is envisioned that the chamber effluent monitoring system can also be used as a safety device in dealing with hazardous gases or vapors. In particular, and with reference to FIG. 5, the chamber effluent monitoring system 8 can be used to monitor the exhaust from a chamber 21 which chamber is a gas cylinder cabinet, a semiconductor manufacturing cleanroom, or a vacuum pump housing.

It is well known that in the IC manufacturing processes, a multitude of hazardous and toxic gases are required. Generally, such gases are kept in cabinets which are continuously evacuated. The cabinet exhaust, i.e., effluent, is drawn through an exhaust line usually to a scrubber system. The inventive chamber effluent monitoring system is particularly well suited for use with these gas cabinets. By disposing an absorption spectroscopy measurement system 8, in the cabinet exhaust 7, a leak detection system providing instantaneous feedback is provided. In particular, a system for detection of HF which has an absorption at a wavelength of 1330 nm, coincident with relatively convenient InGaAsP dioxide emission, is envisioned.

This embodiment is preferably used in conjunction with a visual and/or audio alarm system 22. The alarm system 22 can be activated upon the happening of a certain event, such as the detected absorption or gas concentration exceeding a predefined limit. In addition, the detector can be connected to a valve control system which will automatically close the gas cylinder or other valve(s) to stop the flow of gas. Those skilled in the art will readily be able to design and integrate appropriate alarm systems and controls in the inventive system by use of well known devices, circuits and/or processors and means for their control. Further discussion of this matter is omitted as it is deemed within the scope of persons of ordinary skill in the art. In a further embodiment of the invention, the chamber effluent monitoring system can be used to monitor the environment of a vacuum pump housing.

In another embodiment of the invention, the chamber effluent monitoring system can be applied to the monitoring of cleanroom environments. Because the air exhausted from the cleanroom is generally returned to the cleanroom, hazardous gas leaks or the presence of hazardous vapors in the cleanroom are especially problematic. Therefore, use of an absorption spectroscopy measurement system in the cleanroom exhaust can provide a particularly advantageous leak detection system. As discussed above in reference to the gas cabinets, this system can be used in conjunction with an alarm system.

While the invention has been described in detail with reference to specific embodiments thereof, it will be apparent to one skilled in the art that various changes and modifications can be made, and equivalents employed, without departing from the scope of the appended claims.

What is claimed is:

1. A chamber effluent monitoring system, comprising:
a chamber having an exhaust line connected thereto, the exhaust line including a sample region, wherein substantially all of a chamber effluent passes through the sample region;
an absorption spectroscopy measurement system adapted to measure a concentration of a gas phase molecular species, comprising a light source and a main detector in optical communication with the sample region through one or more light transmissive window, the light source directing a light beam into the sample region through one of the one or more light transmissive window, wherein the light beam passes through the sample region and exits the sample region through one of the one or more light transmissive window, and the main detector responding to the light beam exiting the sample region, wherein the light beam is reflected within the sample region by one or more light reflective surfaces.

2. The chamber effluent monitoring system according to claim 1, wherein the absorption spectroscopy system is a tunable diode laser absorption spectroscopy system.

3. The chamber effluent monitoring system according to claim 1, wherein the sample region is disposed in the exhaust line between and in communication with the chamber and a vacuum pump, a fan, or a scrubber system.

4. The chamber effluent monitoring system according to claim 1, wherein the operation pressure of the processing chamber is about atmospheric pressure.

5. The chamber effluent monitoring system according to claim 1, wherein the light beam passes through a first light transmissive window before entering the sample region, and the light beam passes through a second light transmissive window after passing through the sample region, wherein a light path from the first and second light transmissive window is substantially linear.

6. A. The chamber effluent monitoring system according to claim 1, wherein the sample region is contained within a measurement cell.

7. The chamber effluent monitoring system according to claim 6, wherein the measurement cell is a multipass measurement cell.

8. The chamber effluent monitoring system according to claim 1, wherein the monitoring system further comprises a fluid stabilization line for removing less than about 10% by volume of the total chamber effluent flow.

9. The chamber effluent monitoring system according to claim 1, further comprising an alarm system which activates when the detected gas phase molecular species reaches a predefined detection limit.

10. The chamber effluent monitoring system according to claim 1, wherein the chamber is a vacuum pump housing.

11. The chamber effluent monitoring system according to claim 10, further comprising an alarm system which activates when the detected gas phase molecular species reaches a predefined detection limit.

12. The chamber effluent monitoring system according to claim 1, wherein the chamber is a cleanroom.

13. The chamber effluent monitoring system according to claim 12, further comprising an alarm system which activates when the detected gas phase molecular species reaches a predefined detection limit.

14. The chamber effluent monitoring system according to claim 1, wherein the gas phase molecular species is water vapor, nitric oxide, carbon monoxide or a hydrocarbon.

15. The chamber effluent monitoring system according to claim 14, wherein the gas phase molecular species is water vapor.

16. A chamber effluent monitoring system comprising:
a chamber having an exhaust line connected thereto, the exhaust line including a sample region, wherein substantially all of a chamber effluent passes through the sample region;
an absorption spectroscopy measurement system adapted to measure a concentration of a gas phase molecular species, comprising a light source and a main detector in optical communication with the sample region through one or more light transmissive window, the light source directing a light beam into the sample region through one of the one or more light transmissive window, wherein the light beam passes through the sample region and exits the sample region through one of the one or more light transmissive window, and the main detector responding to the light beam exiting the sample region, wherein the absorption spectroscopy system is a harmonic detection absorption spectroscopy system.

17. The chamber effluent monitoring system according to claim 16, wherein the harmonic used is a second harmonic.

18. The chamber effluent monitoring system according to claim 16, wherein the harmonic used is a fourth harmonic.

19. A chamber effluent monitoring system comprising:
a chamber having an exhaust line connected thereto, the exhaust line including a sample region, wherein substantially all of a chamber effluent passes through the sample region;
an absorption spectroscopy measurement system adapted to measure a concentration of a gas phase molecular species, comprising a light source and a main detector in optical communication with the sample region through one or more light transmissive window, the light source directing a light beam into the sample region through one of the one or more light transmissive window, wherein the light beam passes through the sample region and exits the sample region through one of the one or more light transmissive window, and the main detector responding to the light beam exiting the sample region; and
a second detector providing a reference signal in a portion of the light beam which is reflected by the one of the one or more light transmissive window which the light beam passes into the sample region.

20. The chamber effluent monitoring system according to claim 19, further comprising means for subtracting a reference signal provided by the second detector from a measurement obtained by the main detector.

21. A chamber effuent monitoring system comprising:
a chamber having an exhaust line connected thereto, the exhaust line including a sample region, wherein substantially all of a chamber effuent passes through the sample region;
an absorption spectroscopy measurement system adapted to measure a concentration of a gas phase molecular species, comprising a light source and a main detector in optical communication with the sample region through one or more light transmissive window, the light source directing a light beam into the sample region through one of the one or more light transmissive window, wherein the light beam passes through the sample region and exits the sample region through one of the one or more light transmissive window, and the main detector responding to the light beam exiting the sample region,
wherein the chamber is a gas cylinder cabinet.

22. The chamber effluent monitoring system according to claim 21, further comprising an alarm system which activates when the detected gas phase molecular species reaches a predefined detection limit.

23. A semiconductor processing system, comprising:
a processing chamber for processing a semiconductor substrate, the chamber having an exhaust line connected thereto, the exhaust line including a sample region, wherein substantially all of a chamber effuent passes through the sample region;
an absorption spectroscopy measurement system adapted to measure a concentration of a gas phase molecular species, comprising a light source and a main detector in optical communication with the sample region through one or more light transmissive window, the light source directing a light beam into the sample region through one of the one or more light transmissive window, wherein the light beam passes through the sample region and exit is the sample region through one of the one or more light transmissive window, and the main detector responding to the light beam exiting the sample region, wherein the light beam is reflected within the sample region by one or more light reflective surfaces.

24. The semiconductor processing system according to claim 23, wherein the absorption spectroscopy system is a tunable diode laser absorption spectroscopy system.

25. The semiconductor processing system according to claim 23, wherein the sample region is disposed in the exhaust line between and in communication with the processing chamber and a vacuum pump.

26. The semiconductor processing system according to claim 25, wherein the semiconductor processing system is selected from the group consisting of an etching system, a chemical vapor deposition system, an ion implantation system, a sputtering system and a rapid thermal processing system.

27. The semiconductor processing system according to claim 26, wherein the semiconductor processing system is an etching system selected from an oxide etch and a metal etch system.

28. The semiconductor processing system according to claim 23, wherein the operation pressure of the processing chamber is about atmospheric pressure.

29. The semiconductor processing system according to claim 23, wherein the processing chamber is adapted to contain a plasma atmosphere.

30. The semiconductor processing system according to claim 23, wherein the processing chamber is adapted to contain a reactive gas atmosphere.

31. The semiconductor processing system according to claim 23, wherein the light beam passes through a first light transmissive window before entering the sample region, and the light beam passes through a second light transmissive window after passing through the sample region, wherein a light path from the first and second light transmissive window is substantially linear.

32. The semiconductor processing system according to claim 23, wherein the sample region is contained within a measurement cell.

33. The semiconductor processing system according to claim 32, wherein the measurement cell is a multipass measurement cell.

34. The semiconductor processing system according to claim 23, wherein the monitoring system further comprises a fluid stabilization line for removing less than about 10% by volume of the total chamber effluent flow.

35. The chamber effluent monitoring system according to claim 23, wherein the gas phase molecular species is water vapor, nitric oxide, carbon monoxide or a hydrocarbon.

36. The chamber effuent monitoring system according to claim 35, wherein the gas phase molecular species is water vaper.

37. A semiconductor processing system comprising:
a processing chamber for processing a semiconductor substrate, the chamber having an exhaust line connected thereto, the exhaust line including a sample region, wherein substantially all of a chamber effluent passes through the sample region;
an absorption spectroscopy measurment system adapted to measure a concentration of a gas phase molecular species comprising a light source and a main detector in optical communication with the sample region through one or more light transmissive window, the light source directing a light beam into the sample region through one of the one or more light transmissive window, wherein the light beam passes through the sample region and exits the sample region through one of the one or more light transmissive window, and the main detector responding to the light beam exiting the sample region wherein the absorption spectroscopy system is a harmonic detection absorption spectroscopy system.

38. The semiconductor processing system according to claim 37, wherein the harmonic used is a second harmonic.

39. The semiconductor processing system according to claim 37, wherein the harmonic used is a fourth harmonic.

40. A semiconductor processing system, comprising:
a processing chamber for processing a semiconductor substrate, the chamber having an exhaust line connected thereto, the exhaust line including a sample region, wherein substantially all of a chamber effluent passes through the sample region;
an absorption spectroscopy measurement system adapted to measure a concentration of a gas phase molecular species comprising a light source and a main detector in optical communication with the sample region through one or more light transmissive window, the light source directing a light beam into the sample region through one of the one or more light transmissive window, wherein the light beam passes through the sample region and exits the sample region through one of the one or more light transmissive window, and the main detector responding to the light beam exiting the sample region; and
a second detector for detecting the gas phase molecular species in a portion of the light beam which is reflected by the one of the one or more light transmissive window through which the light beam passes into the sample region.

41. The semiconductor processing system according to claim 40, further comprising means for subtracting a reference signal provided by the second detector from a measurement obtained by the main detector.

42. A method of detecting a gas phase molecular species in a chamber effluent, comprising the steps of:
providing a chamber having an exhaust line connected thereto, the exhaust line including a sample region;
removing substantially all of a chamber effluent from the chamber through the exhaust line thereby passing the removed effluent through the sample region;
detecting a gas phase molecular species with a main detector by an absorption spectroscopy method by directing a light beam from a light source into the sample region through one or more light transmissive window, wherein the light beam passes through the sample region and exits the sample region through one of the one or more light transmissive window, and detecting the light beam exiting the sample region through one of the one or more light transmissive window, wherein the light beam is reflected within the sample region by one or more light reflective surfaces.

43. The method of detecting a gas phase molecular species according to claim 42, wherein the absorption spectroscopy method is a tunable diode laser absorption spectroscopy method.

44. The method of detecting a gas phase molecular species according to claim 42, further comprising detecting gas phase molecular species in a portion of the light beam which is reflected by the one of the one or more light transmissive window through which the light beam passes into the sample region.

45. The method of detecting a gas phase molecular species according to claim 42, wherein the chamber operates at about atmospheric pressure.

46. The method of detecting a gas phase molecular species according to claim 42, wherein the chamber is evacuated by a vacuum pump, a fan, or a scrubber system in communication with the exhaust line.

47. The method of detecting a gas phase molecular species according to claim 42, wherein the chamber is a semiconductor processing chamber which forms a part of a semiconductor processing system.

48. The method of detecting a gas phase molecular species according to claim 47, wherein the semiconductor processing system is selected from the group consisting of an etching system, a chemical vapor deposition system, an ion implantation system, a sputtering system and a rapid thermal processing system.

49. The method of detecting a gas phase molecular species according to claim 48, wherein the semiconductor processing system is an etching system.

50. The method of detecting a gas phase molecular species according to claim 47, wherein the processing chamber contains a plasma atmosphere.

51. The method of detecting a gas phase molecular species according to claim 47, wherein the processing chamber contains a reactive gas atmosphere.

52. The method of detecting a gas phase molecular species according to claim 42, wherein the light beam passes through a first light transmissive window before entering the sample region, and the light beam passes through a second light transmissive window after passing through the sample region, wherein a light path from the first and second light transmissive window is substantially linear.

53. The method for detecting a gas phase molecular species according to claim 42, wherein the sample region is contained within a measurement cell.

54. The method for detecting a gas phase molecular species according to claim 53, wherein the measurement cell is a multipass measurement cell.

55. The method for detecting a gas phase molecular species according to claim 42, further comprising removing less than about 10% by volume of the total effluent flow from the sample region.

56. The method for detecting a gas phase molecular species according to claim 42, further comprising providing an alarm system which activates when the detected gas phase molecular species reaches a predefined detection limit.

57. The method for detecting a gas phase molecular species according to claim 42, wherein the chamber is a gas cylinder cabinet.

58. The method for detecting a gas phase molecular species according to claim 57, further comprising providing an alarm system which activates when the detected gas phase molecular species reaches a predefined detection limit.

59. The method for detecting a gas phase molecular species according to claim 42, wherein the chamber is a vacuum pump housing.

60. The method for detecting a gas phase molecular species according to claim 59, further comprising providing an alarm system which activates when the detected gas phase molecular species reaches a predefined detection limit.

61. The method for detecting a gas phase molecular species according to claim 42, wherein the chamber is a cleanroom.

62. The method for detecting a gas phase molecular species according to claim 61, further comprising providing an alarm system which activates when the detected gas phase molecular species reaches a predefined detection limit.

63. The chamber effuent monitoring system according to claim 42, wherein the gas phase molecular species is water vapor, nitric oxide, carbon monoxide or a hydrocarbon.

64. The chamber effluent monitoring system according to claim 63, wherein the gas phase molecular species is water vapor.

65. A method of detecting a gas phase molecular species in a chamber effluent, comprising the steps of:

providing a chamber having an exhaust line connected thereto, the exhaust line including a sample region;

removing substantially all of a chamber effluent from the chamber through the exhaust line thereby passing the removed effluent through the sample region, detecting a gas phase molecular species with a main detector by an absorption spectroscopy method by directing a light beam from a light source into the sample region through one or more light transmissive window, wherein the light beam passes through the sample region and exits the sample region through one of the one or more light transmissive window, and detecting the light beam exiting the sample region through one of the one or more light transmissive window, wherein the absorption spectroscopy method is a harmonic detection absorption spectroscopy method.

66. The method of detecting a gas phase molecular species according to claim 65, wherein the harmonic used is a second harmonic.

67. The method of detecting a gas phase molecular species according to claim 65, wherein the harmonic used is a fourth harmonic.

68. A method of detecting a gas phase molecular species in a chamber effluent, comprising the steps of:

providing a chamber having an exhaust line connected thereto, the exhaust line including a sample region;

removing substantially all of a chamber effluent from the chamber through the exhaust line thereby passing the removed effluent through the sample region;

detecting a gas phase molecular species with a main detector by an absorption spectroscopy method by directing a light beam from a light source into the sample region through one or more light transmissive window; wherein the light beam passes through the sample region and exits the sample region through one of the one or more light transmissive window, and detecting the light beam exiting the sample region; through one of the one or more light transmissive window, detecting with a second detector the gas phase molecular species in a portion of the light beam which is reflected by the one of the one or more light transmissive window through which the light beam passes into the sample region; and subtracting a reference signal provided by the second detector from a measurement obtained by the main detector.

69. A method of detecting a gas phase molecular species in a chamber effluent, comprising the steps of:

providing a load-lock or wafer transfer chamber in a semiconductor processing tool, the chamber having an exhaust line connected thereto, the exhaust line including a sample region;

removing substantially all of a chamber effluent from the chamber through the exhaust line thereby passing the removed effluent through the sample region;

detecting a gas phase molecular species by an absorption spectroscopy method by directing a light beam from a light source into the sample region through one or more light transmissive window, wherein the light beam passes through the sample region and exits the sample region through one of the one or more light transmissive window, and detecting the light beam exiting the sample region through one of the one or more light transmissive window.

* * * * *

UNITED STATES PATENT AND TRADEMARK OFFICE
CERTIFICATE OF CORRECTION

PATENT NO. : 5,963,336
DATED : October 5, 1999
INVENTOR(S) : McANDREW et al

Page 1 of 2

It is certified that error appears in the above-identified patent and that said Letters Patent is hereby corrected as shown below:

On the cover page, under 'OTHER PUBLICATIONS," line 5, delete "CHI" and insert --HC1--.

Page 2, left column, delete lines 40-43 (duplicate).

Col. 9, line 60, delete the word "should."

Col. 9, line 65, delete "2511" and replace with --25--.

Col. 10, line 22, delete "$BCl_3$ 40 sccm $Cl_2$" and insert therefor --$BCl_3$, 40 sccm $Cl_2$--.

Col. 10, line 32, delete "$2BCl_3 + 3H_2 =$" and insert therefor --$2BCl_3 + 3H_2O =$ --.

Claim 23, line 49, delete "exit is" and insert therefor --exits--.

UNITED STATES PATENT AND TRADEMARK OFFICE
CERTIFICATE OF CORRECTION

PATENT NO. : 5,963,336
DATED : October 5, 1999
INVENTOR(S) : McANDREW et al

Page 2 of 2

It is certified that error appears in the above-identified patent and that said Letters Patent is hereby corrected as shown below:

Claim 37, line 53, delete "region" and insert therefor --region,--.

Claim 68, line 33, delete "region" and insert therefor --region;--.

Claim 68, line 35, delete "window," and insert therefor --window;--.

Signed and Sealed this

Third Day of April, 2001

Attest:

NICHOLAS P. GODICI

*Attesting Officer*   Acting Director of the United States Patent and Trademark Office